(12) United States Patent
Frullini

(10) Patent No.: US 8,093,215 B2
(45) Date of Patent: Jan. 10, 2012

(54) METHOD FOR RESTRUCTURING A BIOLOGICAL TISSUE COMPRISING COLLAGEN FIBRILS AND RELATIVE USES

(76) Inventor: Alessandro Frullini, Reggello (IT)

( * ) Notice: Subject to any disclaimer, the term of this patent is extended or adjusted under 35 U.S.C. 154(b) by 149 days.

(21) Appl. No.: 12/632,180

(22) Filed: Dec. 7, 2009

(65) Prior Publication Data

US 2010/0144746 A1 Jun. 10, 2010

Related U.S. Application Data

(60) Provisional application No. 61/193,557, filed on Dec. 5, 2008.

(30) Foreign Application Priority Data

Aug. 7, 2009 (IT) .............. MI2009A1453

(51) Int. Cl.
*A61K 47/48* (2006.01)
*A61K 31/525* (2006.01)
*A61K 31/35* (2006.01)
(52) U.S. Cl. .................. 514/17.2; 514/251; 514/451
(58) Field of Classification Search .............. 514/17.2, 514/251, 451
See application file for complete search history.

(56) References Cited

U.S. PATENT DOCUMENTS 5,147,514 A * 9/1992 Mechanic ............... 204/157.68

\* cited by examiner

*Primary Examiner* — Raymond Henley, III
(74) *Attorney, Agent, or Firm* — Oblon, Spivak, McClelland, Maier & Neustadt, L.L.P.

(57) ABSTRACT

A method for restructuring a biological tissue comprising collagen fibrils selected from a venous tissue, a cardiac valvular tissue, a cutaneous or subcutaneous tissue, a tissue of a muscular tendon, a tissue of a muscular fascia or a tissue of a muscular aponeurosis, comprising the following operational steps: a) bringing into contact a biological tissue comprising collagen fibrils with a cross-linking chemical composition able to induce cross-linking of collagen fibrils consequent to activation through electromagnetic radiation; b) activating said cross linking chemical composition through exposure to an electromagnetic radiation; c) cross-linking the collagen fibrils of said biological tissue in order to obtain a restructured biological tissue. The method according to the invention can be applied to recover a venous continence and both a venous and a cardiac valve diameter. The method reduces the visibility of cutaneous wrinkles, reinforces or repairs tendons, muscular fascia and aponeurosis as well as to heals surgical or traumatic cutaneous wounds or cutaneous ulcers.

17 Claims, No Drawings

METHOD FOR RESTRUCTURING A BIOLOGICAL TISSUE COMPRISING COLLAGEN FIBRILS AND RELATIVE USES

CROSS-REFERENCE TO RELATED APPLICATIONS

This application claims priority to U.S. Provisional Application No. 61/193,557 filed Dec. 5, 2008 and Italy MI 2009A 001453, filed Aug. 7, 2009, which are hereby incorporated by reference in their entireties.

BACKGROUND OF THE INVENTION

1. Field of the Invention

The present invention refers to a method for restructuring a biological tissue comprising collagen fibrils and relative uses.

In particular, the present invention refers to a method for restructuring a biological tissue comprising collagen fibrils selected from a venous tissue, a cardiac valvular tissue, a cutaneous or sub-cutaneous tissue, a tendon tissue, a tissue of a muscular aponeurosis or a tissue of a muscular fascia.

The aforesaid method is particularly useful to recover the continence and both the venous and cardiac valves diameter.

2. Description of the Related Art

Venous insufficiency is a very common disease spread worldwide. It has been estimated that about 50% of the adult population of the industrialized countries suffers various forms of venous insufficiency.

In the human body the insufficiency of the venous circulation (venous insufficiency) mainly causes the dilatation of the veins and the haematic reflux in the veins. This produces several symptoms and the risk of severe complications.

The dilatation of varicose veins is progressive, since it is mainly due to a loss of structure of the tissues forming the veins (venous tissues).

Venous insufficiency can affect both small and large veins, as well as reticular veins and telangiectasias.

Especially in the case of the telangiectasias, the problem of the venous insufficiency also has aesthetical implications, as telangiectasias are visible on the surface of the skin.

In the state of the art, venous insufficiency of medium-large veins (diameter >0.5 mm) is treated by means of surgery, sclerotherapy and thermal ablation. In the case of the telangiectasias, the treatment of choice is sclerotherapy.

The aforesaid treatments are based either on the surgical removal of the varicose vein or on the induction of a fibrosis of the damaged vascular tissue in order to prevent the haematic reflux in the varicose veins.

Despite the technological progress in this field has made less invasive the above techniques of surgical treatment, they still remain rather aggressive procedures to treat venous insufficiency in the human body.

In this technical field, therefore, it is strongly felt the demand to develop new methods of treatment of damaged vascular tissues to solve the above described pathologies in a less invasive and efficacious way in comparison to the current surgery techniques.

Another very spread pathology in the human being, due to different aetiologies, is the cardiac valvular insufficiency. Likewise to the venous insufficiency, also this pathology is related to a loss of structure of the tissue. Particularly, the damaged tissues are those that constitute the cardiac valves (cardiac valvular tissues), which, due to different reasons, lose their structure with consequent reduction of the number of bonds that link the collagen fibres forming the cardiac valvular tissue.

In the state of the art, the cardiac valvular insufficiency is treated through surgery and pharmacological therapies. Despite the availability of different treatments, the morbidity and the mortality of this pathology still remain quite severe.

Therefore, also for this pathology there is the need to identify new efficacious methods of treatments to solve cardiac valvular insufficiency, which are possibly less invasive than those known in the art.

BRIEF SUMMARY OF THE INVENTION

It is a purpose of the present invention to overcome the drawbacks underlined by the state of the art.

It is an object of the present invention a method for restructuring a biological tissue comprising collagen fibrils selected from a venous tissue, a cardiac valvular tissue, a cutaneous or subcutaneous tissue, a tissue of a muscular tendon, a tissue of a muscular fascia or a tissue of a muscular aponeurosis, said method comprising the following operational phases:

a) bringing into contact a biological tissue comprising collagen fibrils with a cross-linking chemical composition able to induce cross-linking of collagen fibrils upon activation through electromagnetic radiation;

b) activating said cross-linking chemical composition through exposure to an electromagnetic radiation;

c) cross-linking the collagen fibrils of said biological tissue in order to obtain a restructured biological tissue.

The method object of the present invention is particularly proper to restructure the pathological venous tissues of a varicose vein, the valvular tissues of a pathological cardiac valve, the tissues of tendons, the tissues of muscular aponeurosis or fascia, the tissues of cutaneous wrinkles or the tissues of surgical or traumatic wounds.

Thanks to the restructuring effects, the method object of the present invention, when applied to the venous tissues or to the cardiac valve tissues, allows to achieve the recovery of the continence and both the venous and cardiac valvular diameter.

According to this specific embodiment of the present invention, it is a second object of the present invention the use of the method above defined for recovering a venous continence, and both a venous diameter and a cardiac valve diameter.

Another method object of the present invention essentially consists in an "in vivo" chemical transformation of the biological tissues comprising collagen fibrils, such as the tissues of veins, cardiac valves, tendons, muscular fascia or aponeurosis, and cutaneous tissues. However, ex vivo or in vitro methods are also contemplated. Tests on veins as well as on ex vivo segments of veins produced good results.

DETAILED DESCRIPTION OF THE INVENTION

In the present disclosure, by the term "restructuring" it is meant the compaction of the fibres that form a biological tissue comprising collagen fibrils (hereinafter referred to even only as "biological tissue") through formation of chemical bonds (mainly covalent bonds) among said collagen fibrils. As an effect of such a compaction, the biological tissue can change its mechanical properties, such as its elasticity or its mechanical resistance.

The restructuring of the biological tissue is obtained inducing a cross-linking process among the collagen fibrils, particularly among the collagen fibrils of a vein wall, of a damaged cardiac valvular tissue, of a damaged tendon, of a muscular fascia or aponeurosis, or of a tissue belonging to a cutaneous wrinkle or to a surgical or traumatic wound. The cross-linking is obtained by conveying a cross-linking chemical composition (hereinafter referred to also as cross-linking agent) to the proximity of the pathologic tissue, for instance through the blood circulatory system, and subsequently activating such a composition through exposure to electromagnetic radiations.

Preferably, for the activation of the cross-linking agent electromagnetic radiations are used which have wavelengths in the range 300-500 nm and the exposure is done through a laser or a LED device, preferably a blue LED. This range encompasses all intermediate values and subranges, such as 300, 310, 315, 320, 340, 360, 380, 400, 420, 440, 450, 460, 480, 485, 490, 495 and 500 nm.

The activation of the cross-linking agent consists in provoking a photochemical reaction that produces radical active species able to chemically react with the collagen fibrils.

The cross-linking chemical compositions are liquid compositions comprising one or more chemical photoactive substances, such as riboflavin or bioflavonoids. For example, riboflavin or a salt of riboflavin, such as riboflavin phosphate, may be contained in such a solution at a concentration ranging from 0.05 to 5%, more particularly from 0.125% to 1.0% (w/v). Riboflavin formulations are specifically incorporated by reference to Remington, *The Science and Practice of Pharmacy*, $21^{st}$ edition, Chapter 92, Lippincot, Williams & Wilkins, see especially pages 1708-1709. Selection of suitable diluents, excipients or carriers for a photoactive agent such as riboflavin may be made from those described by Kibbe, *Handbook of Pharmaceutical Excipients*, $3^{rd}$ edtion, American Pharm. Assoc. which is hereby incorporated by reference.

Preferably, the bioflavonoids are selected from the group consisting of proanthocyanidin, catechin, epicatechin, epigallo catechin, epicatechin gallate, epigallocatechin gallate, quercetin, tannic acid, and any combination or combinations thereof.

The cross-linking chemical composition can be delivered in the form of a pH-buffered solution or in combination with other suitable pharmaceutical or physiologically acceptable diluents, carriers, excipients or additives, including the intravenous and opthalmic solutions described by Remington, *The Science and Practice of Pharmacy*, $21^{st}$ edition, Chapters 42 and 43, Lippincot, Williams & Wilkins which is incorporated by reference; or the carriers, excipients and diluents described by Kibbe, *Handbook of Pharmaceutical* $3^{rd}$ edtion, American Pharm. Assoc. which is hereby incorporated by reference.

The photoactive agent, the cross-linking chemical composition, and their methods of preparation are well known to the person skilled in the art.

The cross-linking chemical compositions that can be used to achieve the goals of the present invention are activated (i.e. they start to produce active radical species) upon exposure to electromagnetic radiations having wavelengths varying in the range 300-500 nm, preferably in the range 450-480 nm. These values encompass all intermediate values and subranges, as described above.

Although the applicant does not intend in this case to make reference to any particular theory, it is believed that as an effect of the electromagnetic radiation, the cross-linking agent originates radical species, preferably free radicals (i.e. singulet oxygen), able to form chemical bonds which bridge (cross-link) the fibrils of collagen present in the treated biological tissue.

The cross-linking of the collagen fibrils leads to the restructuration of the biological tissue containing the collagen fibrils, with consequent compaction and modification of its mechanical properties.

In the case of the vascular tissue of a varicose vein, through the cross-linking reaction it is provoked the shrinkage of the vascular tissue, reducing the dilatation of the varicose vein up to the extent of recovering a diameter very close to the native diameter of the vein (before the onset of the pathology).

The recovery of the venous diameter through the method object of the present invention, moreover, offers the advantage to be nearly independent from the action of the operator. Unlike the methods of treatment known in the art that either permanently inhibit the functionality of the vascular tissue of the varicose vein (sclerotherapy or ablation) or, even more invasively, surgically remove the whole varicose vein, the method object of the present invention, when used for the recovery of the continence and the venous diameter, offers the advantage of substantially effecting a re-modelling of the damaged vein and to regenerate its native functionality.

The method object of the present invention is particularly suitable to restructure the tissues of varicose vein walls both of medium-large size veins (>0.5 mm and up to over 2 cm) and those of telangiectasias and of reticular veins (diameter <0.5 mm).

In the case of the biological tissues formed of venous or valvular tissues, in a first preferred embodiment of the present invention, the cross linking agent is brought into contact with the venous tissue to be restructured through perfusion with the aid of a vascular catheter. Preferably, it is used a vascular catheter having on its top a source of electromagnetic radiations (for instance, a LED) or it is used a vascular catheter designed for allowing also the passage of an optical fibre able to carry a laser radiation.

The catheter is protected from the environmental radiation, so as to prevent the activation of the cross-linking chemical composition before it comes into contact with the tissue to restructure.

This form of conveyance of the cross-linking agent is particularly preferred in the case of the application of the method object of the present invention to the stabilization of the venous tissues of medium-large size varicose veins and of the tissues of cardiac valves.

In a second preferred embodiment, the cross-linking agent can be conveyed to the venous tissue to restructure through electroporation that allows the trans-dermal passage of molecules. The electroporation is applicable in the case of treatment of superficial vessels, namely those which are close to the skin, such as telangiectasias and reticular veins. This technique allows the trans-dermal administration of the cross-linking agent in order to bring it into contact with the vein to stabilize.

Other methods of epidermal or transdermal, mucosal, or topical delivery as well as formulations for these purposes may be used and are specifically incorporated by reference to Remington, *The Science and Practice of Pharmacy*, $21^{st}$ edition, Chapter 44, Lippincot, Williams & Wilkins, see e.g., pages 882-883 which describe electrically or mechanically modulated delivery and cited references 32-39, which are also incorporated by reference.

In a third embodiment of the method, the cross-linking agent can be conveyed through systemic administration (e.g., orally, intra-dermally, subcutaneously, intramuscularly or intravenously) until it comes into contact with the venous tissue or valvular tissue to restructure.

In the method object of the present invention, the activation of the cross-linking agent can be effected with the aid of a vascular catheter provided at an end with a source of electromagnetic radiation such as a LED. Alternatively, it is possible to use a vascular catheter designed for allowing also the passage of an optical fibre conveying a laser radiation.

Preferably, the same catheter is used to both bring the cross-linking agent into contact with the tissue and activate it in situ.

The wavelengths of the radiation emitted and the type of source to be used (LED or laser) are selected according to the nature of the photoactive substances present in the cross-linking chemical composition, as well known to the person skilled in the art.

To identify the exact position of the vein or of the valve to restructure, in case of deep structures, it is possible to use echodoppler or echocolordoppler analysis. The echodoppler or echocolordoppler analysis also allows following the evolution of the cross-linking reaction of the collagen fibrils and, consequently, the restructuring level and stabilization level of the treated tissue.

Particularly, in the case of the treatment of veins, by the aforesaid analyses it is possible to monitor the progressive reduction of the vein diameter consequent to the restructuration of the treated tissue, in order to obtain the best therapeutical results.

In this way, it is possible to prolong the duration of radiation phase, thus continuing the cross-linking reaction, until the desired diameter is achieved.

Generally, it is possible to obtain restructuration of a venous tissue or of a cardiac valvular tissue by radiating the cross-linking agent, which is in contact with the tissue, with electromagnetic radiations for a few minutes, usually from about 10 to 30 minutes.

If the duration of the radiating phase is prolonged for a longer time, the shrinkage of the varicose vein can continue up to the complete occlusion of the lumen of the vein.

The coarctation of a vein obtained by applying the method object of the present invention to a venous tissues is due to the restructuring and consolidation of the treated tissues, which takes place through a chemical mechanism and it is not due to thermal effects provoked by the heating of the tissue consequent to its exposure to electromagnetic radiations.

In support of the aforesaid, laboratory tests were carried out on segments of a saphenous vein. The tests showed that during the cross-linking reaction the observed increase of temperature is on average of just 0.5° C. and, however, generally lower than 1° C.

In the case of the treatment of telangiectasias, the method object of the present invention can be carried out by radiating with electromagnetic radiations the cross-linking agent, which is in contact with the vein tissue, by acting from the outside of the varicose vein. In fact, since the telangiectasias and the reticular veins are superficial vessels well visible on the skin, it is possible to radiate them with an electromagnetic radiation produced by a source external to the human body. For instance, it is possible to use a UV lamp to radiate the external surface of the skin in correspondence of the vascular tissue to treat. In the same way, an external LED or a laser source may act as an activator of the reaction.

In a further embodiment of the present invention, the method object of the present invention is applicable to restructure cutaneous or subcutaneous tissues.

It is therefore a further object of the present invention the use of the method above described for the treatment of cutaneous wrinkles or for the healing of surgical or traumatic wounds or a cutaneous ulcer. In both these applications the method object of the present invention also produces aesthetical advantages, because induction of the cross-linking of the fibrils of cutaneous collagen provokes the reduction of visibility of cutaneous wrinkles or a better healing of the wounds.

In a further preferred embodiment of the present invention, the method object of the present invention is applicable to restructure a tissue of a damaged or diseased muscular tendon, fascia or aponeurosis. For this purpose the cross-linking chemical composition may be administered in the ways described in the case of the application of the method to the varicose veins.

In case of a tissue belonging to a muscular tendon, fascia or aponeurosis, however, the cross-linking agent may be administered (i.e. conveyed to the tissue to restructure) also intra-operatively. For example, during an arthroscopic procedure, the cross-linking chemical composition can be administered by direct perfusion or direct irrigation and subsequently be activated with electromagnetic radiations through the operative trocar.

Alternatively, during open surgery, the tissue to be restructured can be directly irrigated with the cross-linking chemical composition, and subsequently be activated with electromagnetic radiations.

The method object of the present invention is particularly suitable for the treatment of the tissues of a cardiac valve.

In this embodiment of the invention, the cross-linking chemical composition is brought through a vascular catheter in proximity to the valvular tissue to stabilize.

The cross-linking chemical compositions usable for the treatment of the vascular tissues of cardiac valves, cutaneous tissue, muscular tendons, fascia and aponeurosis are those described above for the application of the method to the varicose veins.

In the case of the tissues of a cardiac valve, the cross-linking agent is conveyed to the tissue to treat through perfusion inside the blood circulatory system by means of a vascular catheter of proper size.

The activation of the cross-linking agent can be produced with the use of a vascular catheter equipped at an end with a source of electromagnetic radiation as a LED. Alternatively, it is possible to use a vascular catheter designed for allowing also the passage of an optical fibre carrying a laser radiation.

The identification of the site in which the vascular tissue of the cardiac valve to restructure is placed, as well as the monitoring of the cross linking of the collagen fibrils effects, can be done through echocardiography.

Even if theoretically the method of the present invention could be used for restructuring the arterial system, the presence of calcium and cholesterol, commonly found in great quantity in the diseased arterial walls, makes very unlikely to obtain a significant therapeutic performance, for example in the treatment of arterial aneurysms.

EXAMPLES

A slightly hypotonic (290 mOsm/l) 100 ml solution (pH 7.25) composition containing the following ingredients was produced:

| 0.125 gr | riboflavin phosphate |
|---|---|
| 20 gr | Dextran T500 |

Carrier/excipient(s) to volume.

Biological tissue containing collagen fibers was contacted with the riboflavin solution and crosslinking was activated by exposure to electromagnetic radiation.

Skin tissue of volunteers was treated with a crosslinking solution containing riboflavin that was administered by electroporation. Various electroporation time periods ranging from 1 min to 15 mins or more and various periods of light exposure ranging from 1 min to 15 mins or more were evaluated.

Good results showing restructuring and/or consolidation of tissue were obtained for veins and ex vivo vein segments.

The invention claimed is:

1. A method for restructuring a biological tissue containing collagen fibrils selected from a venous tissue, a cardiac valvular tissue, a cutaneous tissue, a subcutaneous tissue, a tissue of a muscular tendon, a tissue of a muscular fascia, and a tissue of a muscular aponeurosis, said method comprising the following operational steps:
   a) bringing into contact a biological tissue comprising collagen fibrils with a cross-linking chemical composition able to induce cross-linking of collagen fibrils consequent to activation through electromagnetic radiation;
   b) activating said cross linking chemical composition through exposure to an electromagnetic radiation for a time and under conditions for cross-linking of collagen fibrils to occur, thus
   c) obtaining a restructured biological tissue containing the collagen fibrils cross-linked in step b);
   wherein said cross-linking chemical composition comprises one or more photoactive bioflavonoids selected from the group consisting of proanthocyanidin, catechin, epicatechin, epigallo catechin, epicatechin gallate, epigallocatechin gallate, quercetin, tannic acid, and any combination thereof.

2. The method of claim 1, wherein said biological tissue is a venous tissue or a cardiac valvular tissue and said cross-linking chemical composition is conveyed to the biological tissue to be restructured through perfusion with a vascular catheter.

3. The method of claim 1, wherein said biological tissue is a superficial venous tissue, a cutaneous or subcutaneous tissue and said cross-linking chemical composition is conveyed to the biological tissue to be restructured through electroporation.

4. The method of claim 1, wherein said cross-linking chemical composition is conveyed to the biological tissue to be restructured through systemic administration.

5. The method of claim 1, wherein said biological tissue is a muscular tendon, fascia or aponeurosis tissue and said cross-linking chemical composition is conveyed to said biological tissue, during open surgery or during arthroscopic procedures, by direct irrigation.

6. The method of claim 1, wherein said cross-linking chemical composition comprises one or more photoactive substances.

7. The method of claim 1, wherein said cross-linking chemical composition comprises a photoactive substance that comprises riboflavin.

8. The method of claim 1, wherein said electromagnetic radiation has a wavelength comprised in the range 300-500 nm.

9. The method of claim 8, wherein said electromagnetic radiation has a wavelength within the range of 450-480 nm.

10. The method of claim 1, wherein said electromagnetic radiation is a radiation produced by a laser device.

11. The method of claim 1, wherein said electromagnetic radiation is a radiation produced by a LED device.

12. The method of claim 1, wherein said electromagnetic radiation is a radiation produced by a blue LED device.

13. The method of claim 2, wherein in step b) activation is effected through a vascular catheter with on top a LED device or a vascular catheter adapted to allow also the passage of an optical fibre able to convey a laser radiation, said catheter being inserted into a vein or close to a cardiac valve which contain the pathological tissue to be restructured.

14. The method of claim 1, wherein said biological tissue is a venous tissue that is a telangiectasias and said step b) of activation is effected through radiation of the external surface of the skin in correspondence to the tissue to be restructured.

15. The method of claim 1, wherein restructuring said biological tissue causes or induces recovery of a venous continence and provides both a venous and a cardiac valvular diameter.

16. The method of claim 1, wherein restructuring said biological tissue reduces the visibility of cutaneous wrinkles or induces the healing of a traumatic or surgical wound or a cutaneous ulcer.

17. The method of claim 1, which is performed in vivo.

* * * * *